United States Patent [19]

Urban

[11] Patent Number: 4,971,801
[45] Date of Patent: Nov. 20, 1990

[54] BIOLOGIC RESPONSE MODIFIER

[75] Inventor: Richard W. Urban, Boulder, Colo.

[73] Assignee: Cell Technology, Inc., Boulder, Colo.

[21] Appl. No.: 57,344

[22] Filed: Jun. 2, 1987

Related U.S. Application Data

[63] Continuation-in-part of Ser. No. 872,131, Jun. 9, 1986, abandoned.

[51] Int. Cl.$^5$ .................. A61K 9/27; A61K 45/05; B01J 13/02
[52] U.S. Cl. .................. 424/450; 264/4.3; 424/1.1; 424/85.2; 424/87; 428/402.2; 436/829; 514/885
[58] Field of Search ............... 428/402.2; 424/87, 450; 436/829; 514/885

[56] References Cited

U.S. PATENT DOCUMENTS

| | | | |
|---|---|---|---|
| 4,053,585 | 10/1977 | Allison et al. | 424/89 X |
| 4,241,046 | 12/1980 | Papahadjopoulos et al. | 424/450 X |
| 4,323,561 | 4/1982 | Nowotny | 424/92 X |
| 4,372,949 | 2/1983 | Kodama et al. | 424/450 X |

FOREIGN PATENT DOCUMENTS 0049311  3/1983  Japan ................... 424/450

OTHER PUBLICATIONS

Bergman et al., "New Test for Endotoxin Potency Based Upon Histamine Sensitization in Mice", *Infection and Immunity*, vol. 18, No. 2, Nov. 1977, pp. 352–355.
U.S. Ser. No. 259,742 filed May 1, 1981, Urban, et al.
West et al., "Natural Cytotoxic Reacivity of Human Lymphocytes Against a Myeloid Cell Line: Characterization of Effector Cells", *The Journal of Immunology*, vol. 118, No. 1, Jan. 1977, pp. 355–361.

*Primary Examiner*—Richard D. Lovering
*Attorney, Agent, or Firm*—McCubbrey, Bartels, Meyer & Ward

[57] ABSTRACT

A biologic response modifier is described for human or animal treatment. It comprises natural membrane vesicles and ribosomes in a suspending buffer. The membrane vesicles are comprised of cellular membrane material endogenous to a selected microorganism. The ribosomes are also endogenous to the selected microorganism. The biologic response modifier is substantially free of endotoxin, intact cells, cell walls, and cell membrane fragments. The selected microorganism is one which does not evoke a significant immune deviating response in the patient and is an organism which is substantially non-pathogenic in humans. The selected microorganism is also one in which membrane vesicles are capable of being formed from cell membrane material and which are readily endocytosed by the monocyte-macrophage cell line of the patient.

9 Claims, 9 Drawing Sheets

INVENTION:
- ● 10 ug/ml
- ○ 3 ug/ml
- ■ 1 ug/ml
- □ 0 ug/ml

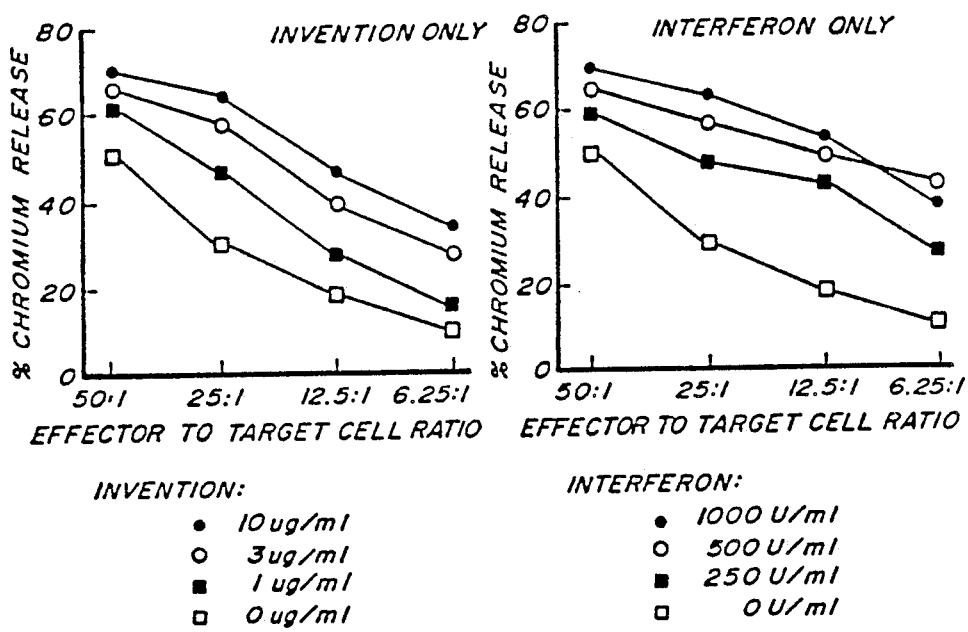
FIG. 2 HUMAN NATURAL KILLER CELL ASSAY
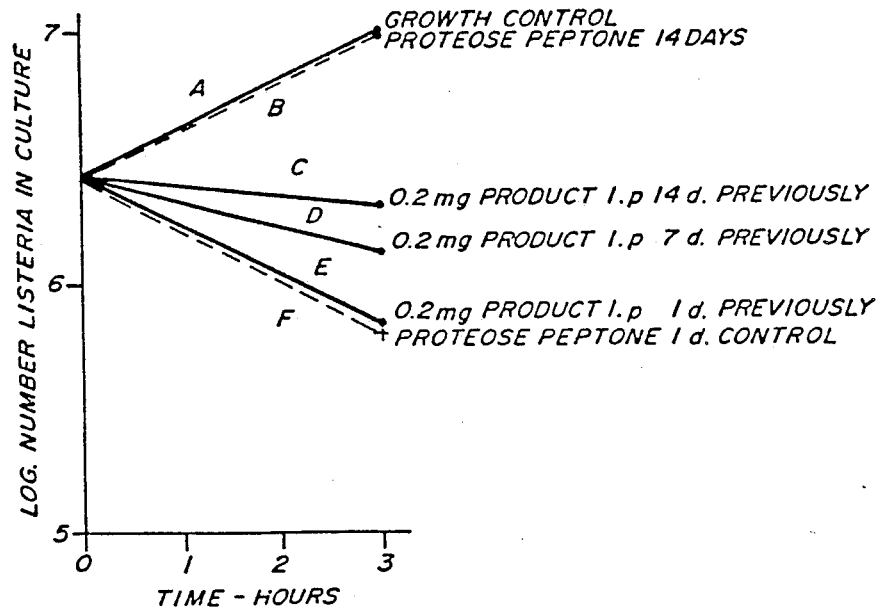
FIG. 3 BACTERIOCIDAL PROPERTIES OF ELICITED PERITONEAL CELLS

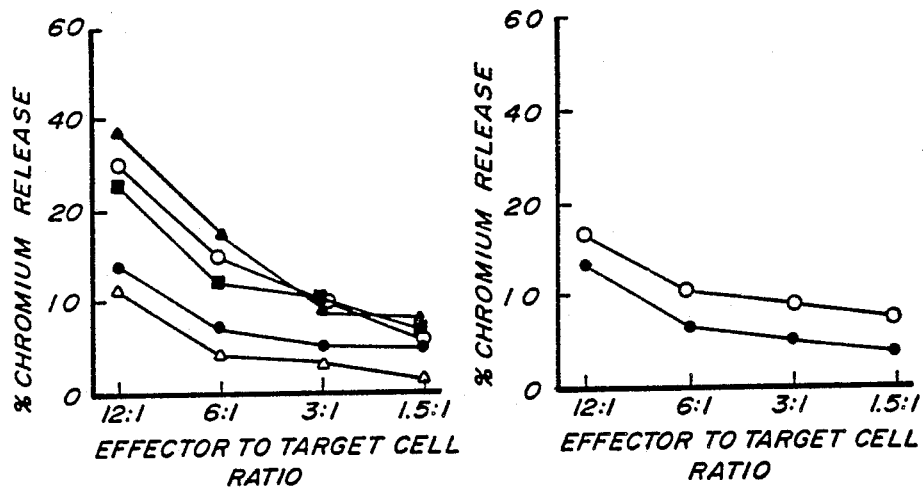
FIG. 4 ADCC ASSAY
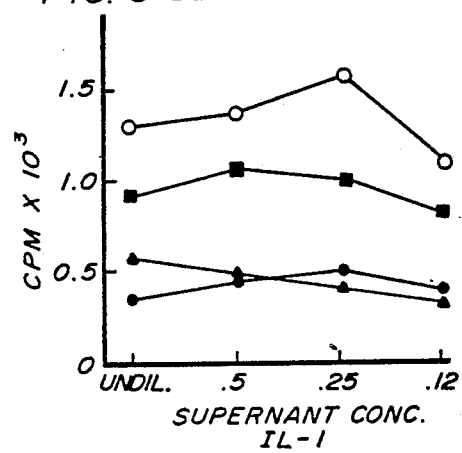
FIG. 5 IL-1 ASSAY
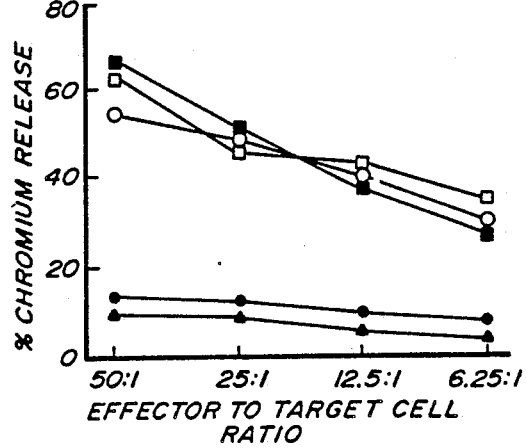
FIG. 6 HUMAN NATURAL KILLER CELL ASSAY

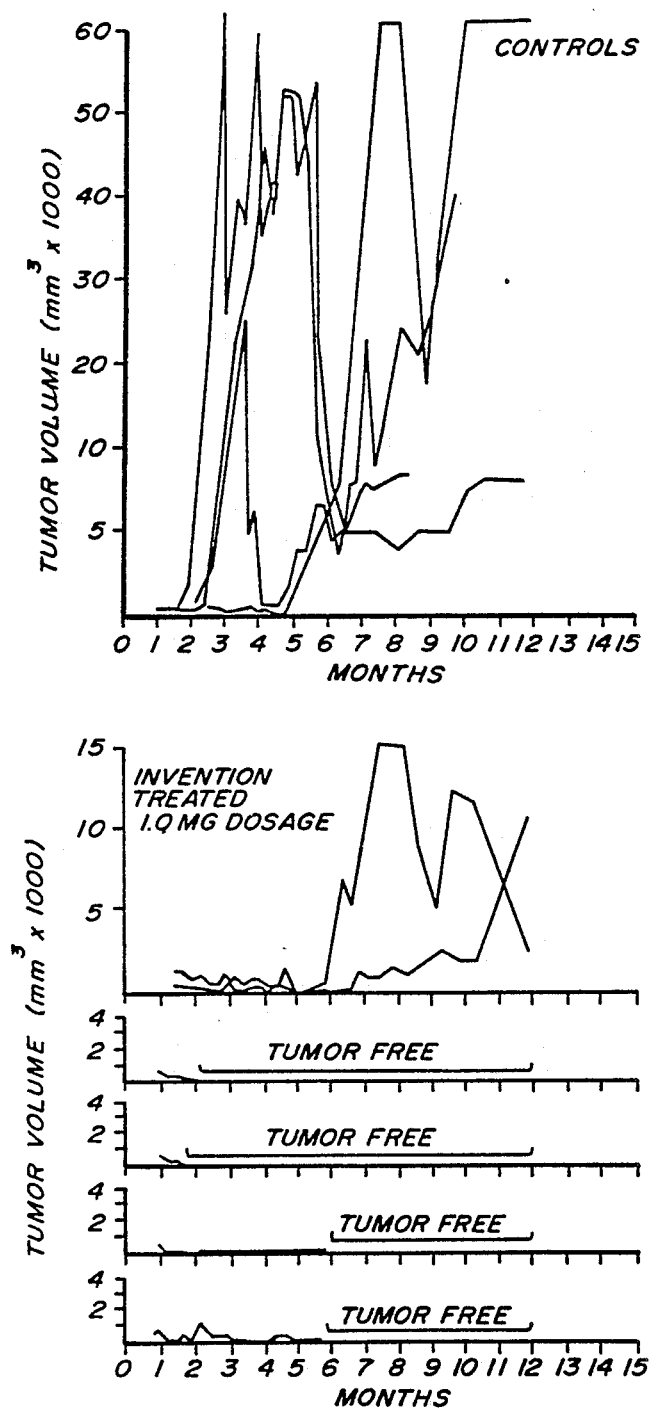
FIG. 7 RAT SQUAMOUS CELL CARCINOMA
RAPID GROWTH TUMOR

FIG. 8 RAT PROSTATIC CARCINOMA
SLOW GROWTH TUMOR
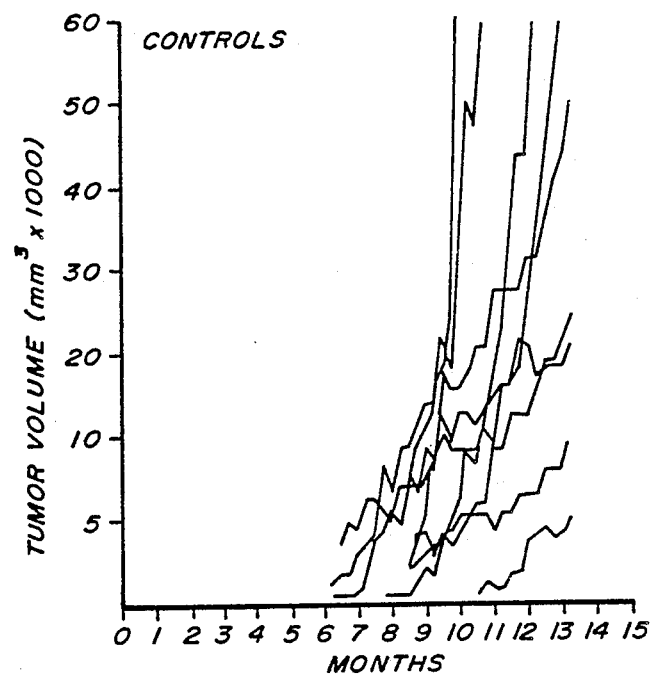
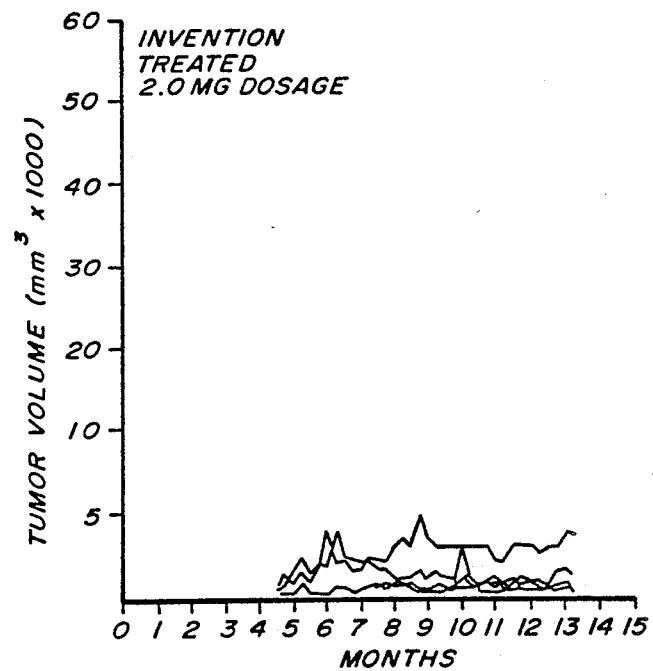

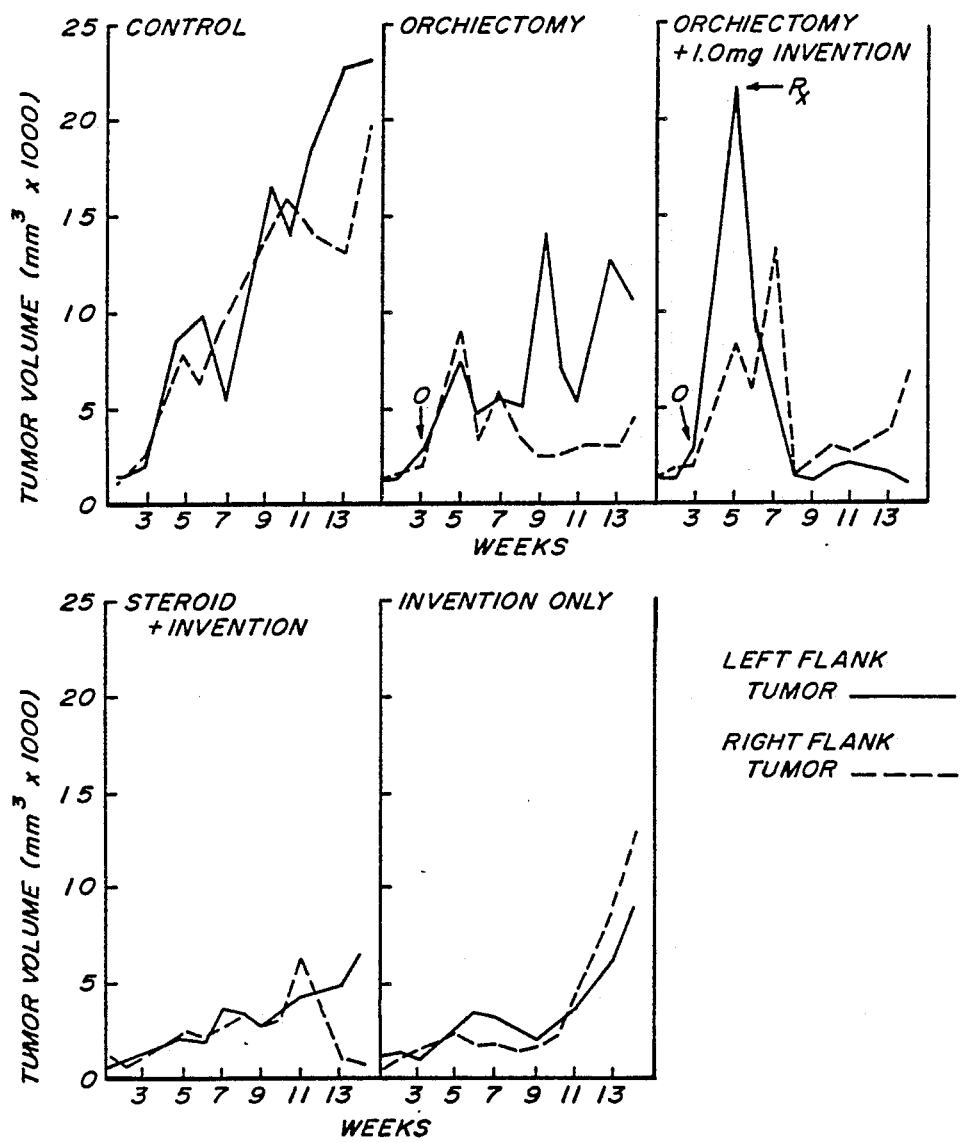
FIG. 9 RAT PROSTATIC ADENOCARCINOMA
BILATERAL TUMORS

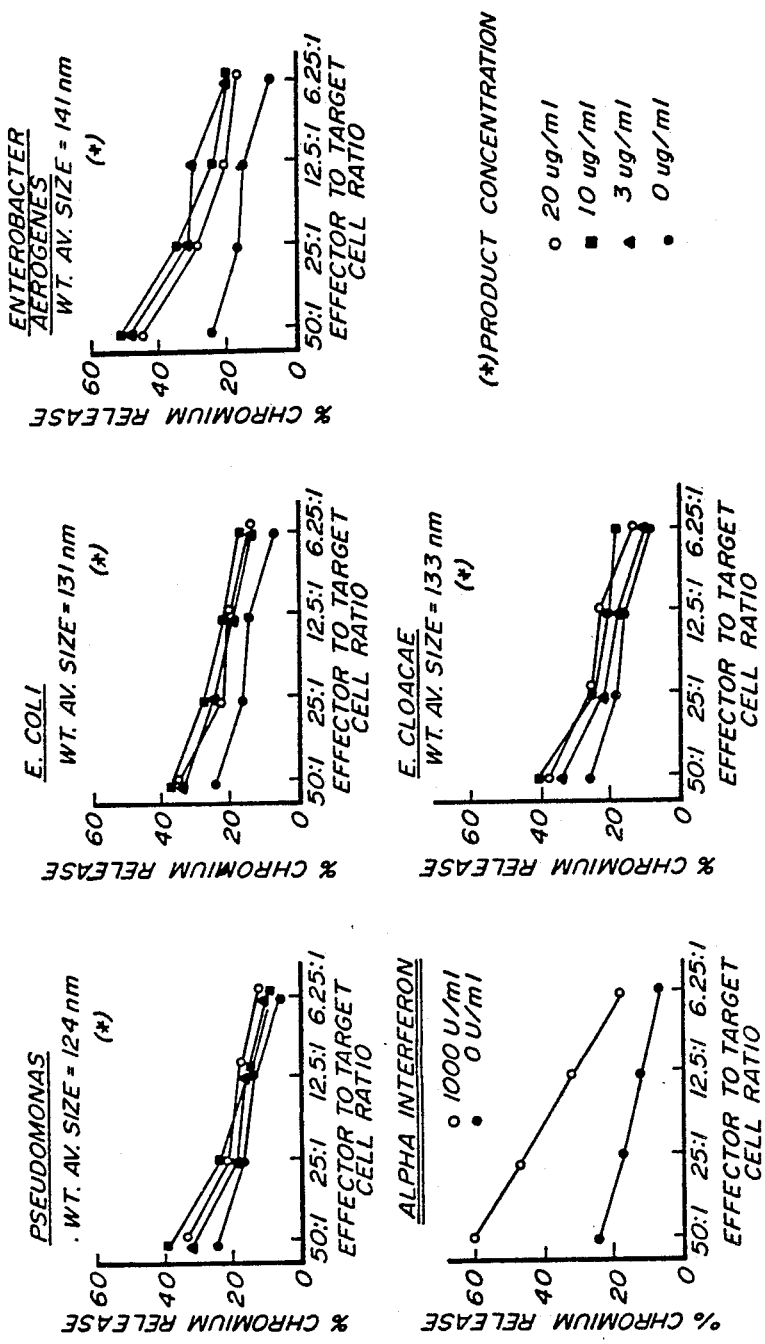
FIG. II IN VITRO COMPARISON OF PRODUCT SOURCES WITH INTERFERON
(HUMAN NK CELL ASSAY, K562 TARGET, 18HR PRODUCT INCUBATION, 4 HR $^{51}$CR RELEASE ASSAY)

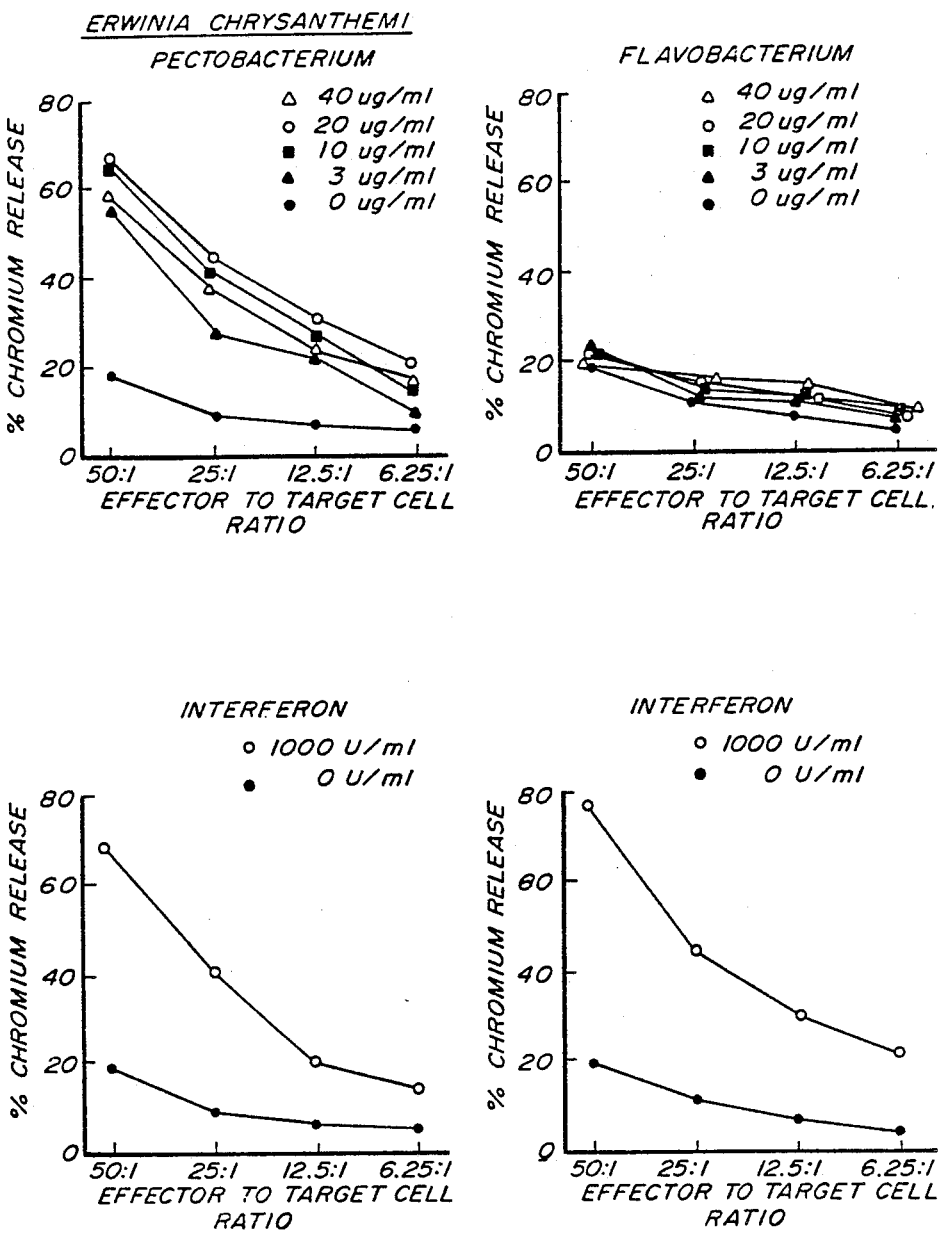
FIG. 12 IN VITRO COMPARISON OF PRODUCT SOURCES WITH INTERFERON
(HUMAN NK CELL ASSAY, K562 TARGET, 18 HR PRODUCT INCUBATION, 4HR $^{51}$CR RELEASE ASSAY)

BIOLOGIC RESPONSE MODIFIER

This application is a Continuation-in-part of U.S. Application Serial No. 872,131, filed June 9, 1986 and abandoned coincident with the filing of this application.

BACKGROUND OF THE INVENTION

This invention relates generally to a pharmaceutical product having immunomodulating properties. More particularly, the invention relates to a biologic response modifier (BRM), defined as an agent that modifies the relationship between a disease and host by modifying the host's biological response to the disease with resultant therapeutic effects. The BRMs can be divided into two categories: (1) biologic or chemical agents that can stimulate or otherwise alter one or more of the host's resistance mechanisms and (2) purified cellular products that demonstrate direct effects on a particular disease. The first group of BRMs, in which the present invention falls, consists of agents that activate, increase, or otherwise modify host immunologic reactivity and are generally referred to as immunomodulators.

A BRM may be used alone, or in combination with other agents, to enhance resistance to or recovery from invasion by pathogens, to modify or induce tolerance to grafts of foreign tissue, to enhance tumor rejection or stabilization and to inhibit tumor recurrences following other forms of therapy, to restore normal helper-suppressor mechanisms, or otherwise promote a normal immune response.

A wide variety of immunomodulators/ immunoadjuvants has been developed since the early 1900s. The vast majority of these agents are of microbial (bacterial/fungal) origin with the most popular ones being derived from the Corynebacteria, Mycobacteria and Nocardia genera (CMN organisms). The various immunoadjuvants are comprised of either intact viable cells, dead cells, cell walls, various cell wall fractions, endotoxin, various types of polysaccharides, or subcellular fractions such as ribonucleic acid or ribosomes. Although all of these agents have demonstrated immune potentiating/modulating/adjuvant activity in tissue culture, animals, and humans, against infectious and neoplastic disease, they are universally plagued with inconsistencies in production and composition, and have moderate to severe toxicity. Relative to the treatment of neoplasia, only a few of these agents have thus far been useful in the treatment of established disease. Moreover, these agents typically demonstrate loss of activity with repeated use (anergy), hypersensitivity reactions, development of chronic inflammatory conditions, and/or the development of various other undesirable conditions.

Because of the inability to chemically define these agents due to their impurity and/or complexity, and in an attempt to reduce the variability of the immune responses and toxic complications, a number of investigators either have extracted various specific fractions from these sources or have synthesized various components demonstrating immunologic activity. Examples of specific fractions that have been investigated include the cell wall fraction muramyl tripeptide, staphlococcal protein A, various polysaccharides, the RNA fraction[1], and the ribosomal fraction[2-5].

With respect to the ribosomal fraction, the mechanism of action differs according to the ribosome source. Although the majority of ribosomal vaccines require adjuvant for activity, ribosomal vaccines prepared from *Staphylococcus aureus* and *Neisseria meningitis* do not.[2] In addition, ribosomal vaccines prepared from *Mycobacterium tuberculosis*[3] and *Salmonella typhimurium*[4] appear to induce a cell-mediated response, whereas those prepared from *Streptococcus pneumoniae* and *Streptococcus pyogenes* mediate a humoral response.[5] Even though the extracted ribosomal fraction is, theoretically, the active agent, considerable controversy exists in many cases as to whether other cell components (RNA, protein, endotoxin, cell wall) present as contaminants are responsible for the observed immune reactivity.

Known cell fraction vaccines may sometimes be appropriate for the prophylactic or therapeutic treatment of infectious disease. However, they are, for several reasons, inappropriate for use as nonsensitizing general immunomodulators for the treatment of neoplastic disease. The presence of cell wall, endotoxin, or poorly degradable components often results in toxicities similar to those obtained with the intact organisms. Moreover, undesired immune suppressive and complex immune responses may be elicited since such vaccines are typically derived from organisms which are part of or which readily cross-react (common antigens) with the host's own microflora. Such vaccines also typically contain fractions having physical and/or chemical characteristics which may be suboptimal for general immune potentiating activity.

Urban, et al.[6] reported on the ability of polyribosomes (aggregates of ribosomes) obtained from a specific bacterial organism to suppress the development of cutaneous SaD2 fibrosarcomas in DBA/2 mice. Polyribosome fractions were obtained from cell cultures by lysing the cells osmotically or mechanically (depending on the type of bacteria), followed by differential centrifugation. Although the effect on the SaD2 murine tumor was positive, the mechanism of the induced biological response could not be determined from the data. Although toxicity was significantly low, the process described by Urban, et al. resulted in an extreme variation in polysome profile (size distribution) and a very low product yield. Consistency of quality, stability and effectiveness was not established.

Kirsh, et al.[7] have reported on immune stimulation and modulation via encapsulation of specific antigens or biologic response modifiers in liposomes. Liposomes containing drugs have been utilized for the treatment of metastatic cancer.[8] However, the treatment of neoplastic disease (cancer) with biologic response modifiers alone or encapsulated in liposomes far been discouraging. Although encapsulated BRMs surpass non-encapsulated BRMs in efficacy, the limitation of therapeutic benefit may be due to immune activation being limited to the macrophage. The numbers of macrophages in these cases have been too low to effectively mediate, by themselves, the destruction of large tumor burdens.

It is an object of the present invention to provide an improved biologic response modifier.

It is another object of the invention to provide an improved biologic response modifier which exhibits minimal toxicity and immune suppression.

Another object of the invention is to provide an improved biologic response modifier which is capable of manufacture with consistent quality, stability and effectiveness.

Still another object of the invention is to provide a method for making the foregoing biologic response modifier which provides consistent quality and high yield.

Other objects of the invention will become apparent to those skilled in the art from the following description, taken in connection with the accompanying drawings.

BRIEF DESCRIPTION OF THE FIGURES

FIG. 2 is a graph illustrating a human natural killer cell assay upon administration of the biologic response modifier of the invention as compared with administration of leukocyte interferon.

FIG. 3 is a graph depicting a standard assay which demonstrates the bacteriocidal properties of the BRM of the invention.

FIG. 4 is a comparison of an antibody-dependent cellular cytotoxicity (ADCC) assay upon administration of the biologic response modifier of the invention as compared with administration of leukocyte interferon.

FIG. 5 is a graph illustrating the induction of interleukin 1 (IL-1) utilizing the biologic response modifier of the invention.

FIG. 6 is a graph illustrating, on natural killer (NK) cell activity, the effect of depleting various populations of human peripheral blood mononuclear cells. (This study demonstrates loss of NK cell activity upon removal of NK cells but not upon removal of B-cells or T-cells when utilizing the biologic response modifier of the invention. Removal of monocytes (not shown) also eliminates the effect, suggesting that the NK cell activity is mediated via the monocyte-macrophage population.)

FIG. 7 illustrates the results of in vivo studies of use of the invention on rat prostatic squamous cell carcinoma (R3327A) (rapid growth).

FIG. 8 illustrates the results of in vivo studies of rat prostatic carcinoma (R3327H) (slow growth).

FIG. 9 illustrates the results of in vivo studies of bilateral rat prostatic adenocarcinoma (R3327CF), also showing results in connection with other treatments.

FIG. 11 is a series of graphs depicting natural killer cell assays comparing, with alpha interferon, the effectiveness of preparations made from the source microorganisms *Pseudomonas, E. coli, Enterobacter aerogenes,* and *E. chloacae.*

FIG. 12 is a series of graphs depicting natural killer cell assays, comparing, with interferon, the effectiveness of preparations made from the source microorganisms *Erwinia chrysanthemi* and *Flavobacterium.*

SUMMARY OF THE INVENTION

Very generally, the biologic response modifier of the invention comprises natural membrane vesicles and ribosomes in a suspending buffer. The vesicles are comprised of cellular membrane material endogenous to a selected organism. The ribosomes are also endogenous to the selected organism. The biologic response modifier is substantially free of intact cells, and has tolerable levels of endotoxin, cell walls, and cell membrane fragments. The selected organism is one which does not evoke an immune suppressing response, is non-pathogenic in humans, and is one from which membrane vesicles are capable of being formed from cell membrane material and which vesicles are readily endocytosed by the monocyte-macrophage cell line. The vesicle population of the biologic response modifier exhibits a mean diameter of at least 180 nm on particle size analysis.

Figure 10:
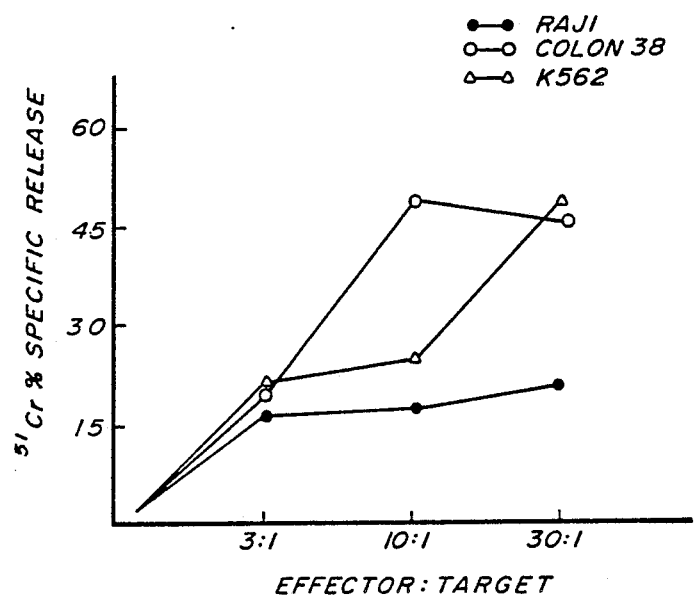
FIG. 10 is a summary of data acquired from the treatment of terminal cancer patients illustrating the effectiveness of the patient's peripheral blood mononuclear cells to kill specific tumor target cells 24 hours after in vivo administration of the invention. The results are comparable to the in vitro activation of human peripheral blood mononuclear cells with interleukin II.

The invention is capable of directly activating cells of the monocyte-macrophage cell line. Activation of the monocyte-macrophage, or cells of the monocyte-macrophage cell line, results in the induction of monocyte-macrophage mediated bacteriocidal activities (FIG. 3) and tumor cytotoxicity (Table 3), altered levels of various white blood cells involved in immune function (e.g., monocytes, neutrophils (Table 4)), human in vivo induction of tumor target (K562, Raji, Co:38) cytotoxicity (FIG. 10), induction of natural killer cell mediated cytotoxicity (FIG. 2), induction of antibody dependent cellular cytotoxicity (FIG. 4), and induction of the release of interleukin I (IL-I) (FIG. 5) and possibly interleukin II (IL-II) (FIG. 10).

Definitions

For the purpose of preciseness, the following terms used in this specification and the appended claims are defined:

"Non-toxic" means within a level of toxicity which is tolerable by the mammalian host receiving biologic response modifier therapy.

"Non-immunogenic" means evoking a sufficiently low immunogenic response, or no response at all, such that undesired immune deviating, chronic inflammatory and hypersensitivity responses are not elicited, significantly, in the mammalian host.

"Mean diameter" means the mean diameter of MSD Particle Size Distribution Analysis as measured on a BI-90 (Brookhaven Instrument Corp.) particle sizer. This measurement involves an intensity weighting of the size averaging process and is explained more fully in the Operator's Manual for the instrument, Chapter 6, incorporated herein by reference.

"Substantially non-pathogenic in humans" means not or rarely associated with disease in humans of normal health. Since most microorganisms are capable of causing opportunistic infections under the right circumstances, such as in persons whose immune system has been compromised, this definition excludes only those organisms which typically cause non-opportunistic infections.

"Tolerable level of endotoxin, cell walls, and cell membrane fragments" means that any such factions, if present, have a low enough level of biologic activity to maintain a non-toxic characteristic as defined herein.

"Immune suppressing response" means an immune response which so attenuates the effect of the desired immune response as to be unacceptable for medical purposes.

"Natural membrane vesicles" means membrane vesicles prepared from membranes which are derived from living or dead natural cells.

DETAILED DESCRIPTION OF THE INVENTION

Although scientific evidence is unavailable to clarify the reasons for the observed efficacy of the biologic response modifier of the invention, it is clear that the biologic response modifier of the invention possesses certain distinguishing characteristics. Thus, it is clear that the biologic response modifier of the invention contains two distinct particle classes, namely natural membrane vesicles and ribosomes. The ribosomes may exist as monomers or as larger polymers, but the mean diameter of the ribosome population is less than the mean diameter of the membrane vesicle population. The relative amounts of the two populations appear to affect the efficacy of the product as determined by standard NK cell assays conducted in vitro. Also, of course, the relative populations affect the measured mean diameter of the total population of particles.

It has also been observed that the size of the vesicles in the vesicle population have an effect on the efficacy of the biologic response modifier of the invention. Thus, in a preferred form of the invention, substantially all of the vesicles exceed 110 nm in diameter and the mean diameter of the vesicle population is at least 180 nm and is preferably about 210 nm.

Figure 1:
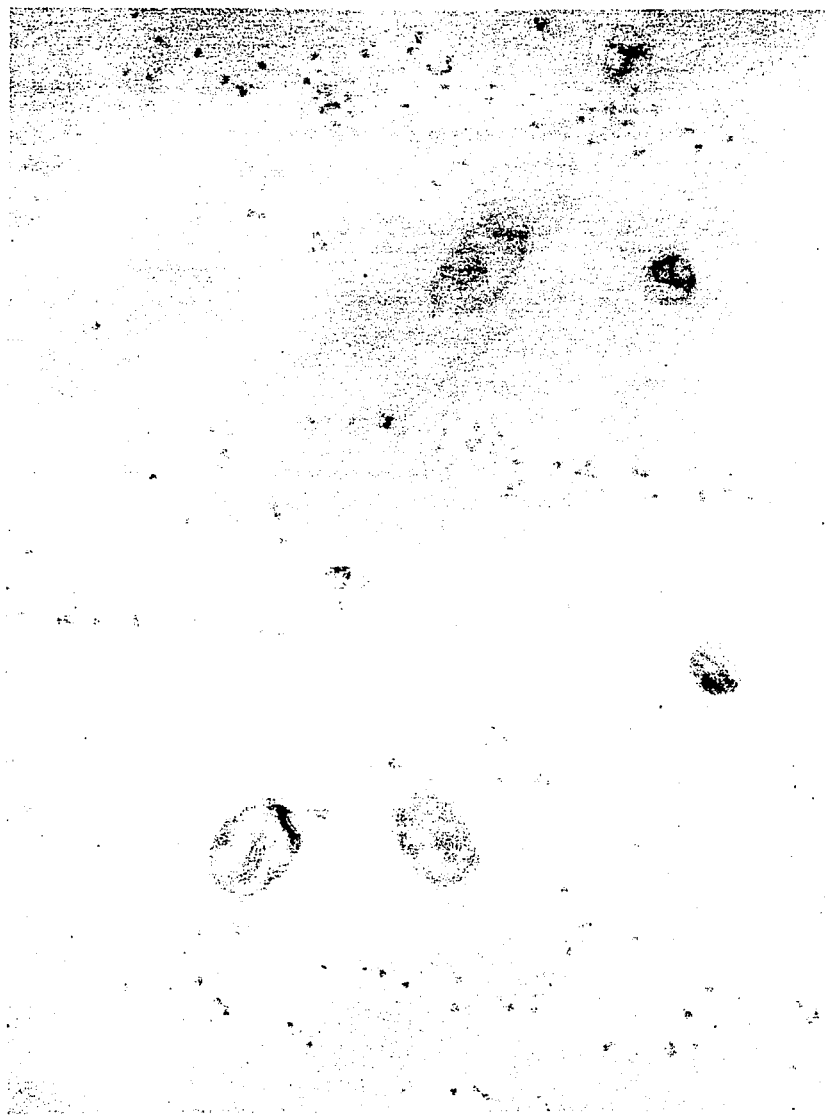
FIG. 1 is an electron micrograph depicting the biologic response modifier of the invention at approximately 82,000 magnification.

FIG. 1 is an electron micrograph, enlarged approximately 82,000 times, showing the cross-sectional appearance of the membrane vesicles and also showing free ribosomes of various particle size (i.e. monomers and small polymers). The manufactured vesicles have been measured by two methods: (1) direct measurement of cross-sectional diameters as seen in electron micrographs; and (2) mathematically, using measurement of particle diffusion coefficients obtained from light scatter analysis using a BI90 (Brookhaven Instrument Corp.) particle sizer.

In a preferred form of the invention, the membrane vesicles and the associated ribosomes are derived from (i.e. endogenous to) the gram negative bacterium *Serratia marcescens*. *Serratia marcescens* is a well known organism and many strains are available from a number of sources. Sixty strains are available from the American Type Culture Collection, Rockville, Md. 20852. This organism provides a particularly suitable source for manufacturing the product exhibiting a high level of immunomodulating/immuno-therapeutic activity as compared to other bacterial sources, and is substantially free of toxicity.

The specific *Serratia marcescens* strains actually utilized in developing the data set forth below were:

Serratia 2000 (SM2000) Cell Technology (Boulder, Colo., USA) in-house strain pigmented and non-pigmented variants;

Serratia MSC unknown origin from stock culture at Metropolitan State College (Denver, Colo., USA);

*Serratia marcescens* ATCC #60; and

*Serratia marcescens* CU unknown origin from stock culture at University of Colorado (Boulder, Colo., USA).

The desired bacterial membrane vesicles and ribosomes may be conveniently and economically isolated from a suitable source of stationary phase or log phase *S. marcescens* bacterial cells by means of the method of the invention, which is a simple, rapid and reproducible procedure. Reagents are employed which supply the necessary conditions for the maintenance of the integrity and conformation of the specific fractions isolated. Any reagents which might by themselves be toxic (unacceptably tolerated) or in any way influence or otherwise alter an immune response are avoided.

The preferred isolation procedure involves cultivating a seed lot of the bacterial cells in a suitable culture medium at a suitable temperature (30°–40° C.) to a log phase culture (a given phase of growth is related to final product yield and consistency as is the final density of viable cells per unit volume of culture medium processed; rapidly chilling the log phase culture to 0°–4° C.; harvesting the bacterial cells; washing and suspending the harvested cells to a prescribed density in a suitable buffering system which maintains an environment suitable for the formation and stability of the membrane vesicles and for the stability of the ribosomes; breaking open (lysing) the cells in a suitable cell disrupter or French pressure cell to produce membrane vesicles with a diameter in excess of about 110 nm or 0.11 microns (disruption of the cells occurs in the presence of a suitable detergent for facilitating inner membrane or endotoxin dissociation); clearing the bacterial cell lysates of cellular debris, including intact cells, cell wall fragments, and large ribosomal aggregates and polysomes, layering the cleared cellular lysate containing the vesicles and remaining soluble cellular constituents on an appropriate linear or discontinuous density gradient material which is non-toxic (acceptable tolerance), and non-immunogenic; pelleting the appropriate vesicle and ribosome fractions while minimizing the pelleting of unacceptable smaller fractions; aseptically removing the density gradient material; rinsing the pelleted fraction and then uniformly resuspending the membrane vesicles and ribosomes with minimal disruption in an appropriate buffering system.

In carrying out the above described isolation procedure, rapid chilling of the log phase culture to 0°–4° C. may be carried out by any suitable means, such as, for example, by employing a dry ice-alcohol mixture, an acetone-ice mixture, an alcohol-ice mixture, or special devices such as cooling coils. All subsequent steps are preferably carried out at 0°–4° C. Cell harvesting may be carried out by centrifugation, or cell harvesters/concentrators may be used instead. Clearing of cellular debris and isolation of the specific vesicle fraction may all be carried out by centrifugation.

The membrane vesicle and ribosomal fractions may also be isolated via employment of size-exclusion chromatography. Cleared cell lysate is passed through gels such as Sephadex G-25, G-50, G-100, G-200, Sepharose 2B, Sephacryl S-200, Sephacryl-50, Biogel P-30, Sepharose 4B, TSK HW-75F Fractogel (all trademarks), or any other similar gels having a molecular exclusion limit of roughly 5,000 to 40,000,000 daltons. Cleared cell lysate is loaded onto a presaturated column. The membrane vesicles appear in the void volume while other proteins, cell debris and detergent are eluted in larger volumes. For example, 1 ml of cleared lysate is loaded onto a 10 ml G-100 Sephadex (TM) column and eluted with buffer. The membrane vesicles appear in the void volume. Other proteins and cell products elute at higher volumes. The product can be repeatedly passed over the column but each passage causes at least a twofold dilution of the sample. The product can be (if necessary) concentrated by ultra-filtration or by centrifugation.

Columns and gels can be prepared in sterile and endotoxin-free manners as specified by the gel manufacturers. For example, Sephadex (TM) gel can be autoclaved at 15 lb/in$^2$ on liquid cycle for 15 minutes. The gel material is allowed to cool to room temperature, is poured into a microcleaned endotoxin-free column and packed at a flow rate of 8–30 ml/hr. The effluent of the column can be checked for endotoxin contamination by the well-known LAL assay.

A suitable buffering system for isolation of the membrane vesicle and ribosomal fractions of the invention is comprised of 20 mM $MgSO_4$, 50 mM $NH_4Cl$, and 20 mM Tris HCl, pH 7.6; and for final suspension, the above buffer or Tris or phosphate buffered isotonic saline of the same pH may be used. The magnesium sulphate may be replaced by any other suitable source of magnesium ions, such as magnesium acetate. The components of the buffering system and their specific concentrations may be varied as long as the integrity of the membrane vesicle and ribosomal fraction isolated via the described procedure is maintained. Tris-HCl may be replaced by Trizma 7.1, Trizma 7.2, or any other suitable Tris buffering agent adjusted to pH 7.0 to 7.6. Any buffering system/agent that does not alter the integrity of the membrane vesicles or ribosomes and which is acceptably tolerated by tissues and the intact organism at the concentration employed may be utilized. The actual pH of the buffering system must be compatible with the maintenance of the vesicles and ribosomes, and of the tissues into which the material is injected.

The cells are lysed in such a way as to cause fracture and shearing of the cell, so as to produce the membrane vesicles. Any suitable technique may be employed which will produce the desired membrane vesicles. It has been found preferable to effect the lysis mechanically, for example, in a cell disrupter or a French pressure cell. The mechanical lysis conducted is operated so as to provide enough shear to produce the membrane vesicles and associated ribosomes.

A satisfactory lysing procedure is to employ a Microfluidizer 110, Model 110T from Biotechnology Development Corporation. Microfluidization is the dynamic interaction of two bacterial fluid streams in precisely defined microchannels resulting in the lysing of the bacteria and in the production of uniformly sized membrane vesicles. The bacterial suspension is pumped through the interaction chamber of the microfluidizer at 10,000 to 14,000 psi 6 to 12 times to ensure lysis of the cells and the proper vesicle size range. Optimal conditions are 11,000 psi and nine passes. A suitable cell concentration for microfluidization (vol. cell: vol. cell + vol. buffer) is 0.16.

Where a French pressure cell is used, the operating pressure of the cell should provide a high degree of cellular disruption such that the desired membrane vesicles are formed. A preferred pressure is about 12,000 psi, but pressures in the range of about 10,000 psi to about 35,000 psi are also satisfactory.

A satisfactory French pressure cell is model no. J43339, 40,000 psi rating available from S.L.M. Instruments in Champagne, Ill. An automatic hydraulic press is used to pressurize the cell, preferably at a nominal level of 12,000 psi. The pressure is not allowed to oscillate more than about ±500 psi. Pressures below 12,000 psi (cell pressure) result in substantially less lysis of the cells and in progressively more of the vesicles being below about 110 nm. The outlet valve is opened to allow an outflow of lysate at a rate of about 20 ml per minute. However, an outflow as low as 1.0 ml/minute is also acceptable (range 1–40 ml/minute). Flow rate must be such as to provide vesicles of the specified size range. Suitable cell concentration range for passage in the French pressure cell is (vol.cells: vol.cells + vol.buffer) 0.16 to 0.32.

A detergent should be utilized to dissociate endotoxins and membrane fragments to smaller, more easily separable particles. A particularly suitable nontoxic detergent for use in the cell lysis procedure is sodium deoxycholate. A suitable (deoxycholate) concentration range is 0.15–0.3% final. A non-toxic (well tolerated) detergent should be utilized.

The product of the invention has tolerable levels of cell walls; biologically active endotoxin; said cell membrane fragments; as indicated by various biological assays and human toxicity studies. The product is also free of intact cells. In order to accomplish this, two centrifugation steps are preferably employed. The first centrifugation is as follows:

(a) Twenty milliliters of cold bacterial cell lysate is collected during the lytic process in a 0°–1° C., microcleaned, sterile, Beckman #30 rotor polycarbonate bottle. The number of such centrifuge bottles prepared is determined by the quantity of final product to be manufactured. This volume of lysate represents a running, vertical $R_{min}$ of 72 mm and a useful $R_{max}$ of 95 mm. The tubes are centrifuged in a prechilled (0°–4° C.) Beckman #30 rotor at 16,000 rpm, using normal acceleration in a Beckman ultracentrifuge. The centrifugation time is such that the average S value cleared to between the $R_{min}$ and $R_{max}$ values is 600 Centrifugation times resulting in lysate average S values below 600 result in significant product loss. Average S values significantly above 600 (e.g. 900S) run the risk of final product contamination with various toxic cellular components. As long as product contamination does not occur, the higher average S values will provide increased product yield. A usable safe range is about 600–800 S [average]. Using a Beckman #30 rotor, polycarbonate bottles, and a lysate volume of 20.0 ml, an average 600S cleared lysate is obtained with an $W^2t$ of $3.55 \times 10^9$ (20 minutes run at 16,000 rpm + 3 min to attain speed with normal acceleration). This procedure removes intact viable and dead cells, and all large cell fragments and subcellular components including large polysome aggregates having an average S value greater than 600. The centrifugation procedure is carried out at 0°–4° C.. The brake is released at 500–1000 rpm and the rotor allowed to come to a complete stop. To prevent swirling of tube contents the brake should not be released below 500 rpm. Release of the brake at rpm's higher than 1000 only prolongs the production process. Other rotors and centrifuges may be utilized (e.g., Sorvall Superspeed and an SS-34 rotor, Beckman Superspeed centrifuges and equivalent or larger capacity rotors), as long as the methodology is equivalent.

(b) All procedures are carried out at 0°–4° C.. The cleared lysate is carefully and aseptically harvested (15–16 ml of total volume) with a cold sterile, nonpyrogenic syringe and 18G spinal needle (or equivalent). The tip of the needle is kept a few millimeters below the lysate surface during harvest and great care must be taken not to touch the sides of the centrifuge bottle and not to disturb the pellet. The harvested lysate is immediately passed through a cold 0.45 micron filter (e.g. Millex-HA, Millipore) and collected in a cold, sterile, nonpyrogenic, preferably non-binding plastic/glass tube(s).

After the first centrifugation step and filtration, the lysate is then immediately layered on sucrose gradients in microcleaned, sterile, cold, polycarbonate centrifuge bottles. The diluent used is the buffering system described above. The layered gradients are then subjected to the second centrifugation step.

Product isolation parameters are as follows:

(1) Basic product yield (1–1.2 mg product/1.0 ml cleared lysate layered/gradient).

50 Beckman Rotor:

gradient: 4–5 ml 15% w/w sucrose layered on 3.0 ml 30% w/w sucrose in polycarbonate bottles—sharp interface. The sucrose is sterile and endotoxin negative as determined by a quantitative Limulus assay.

Sample size: 1.0 ml cleared/filtered lysate

Centrifugation: 0°–4° C.; slow acceleration; 38,000 rpm, 60 minutes at speed.

(2) To increase the amount of product isolated per centrifugation, the following rotors may be used:

30 Beckman Rotor:

gradient: 11.0 ml 15% w/w sucrose (depending on volume of lysate layered) layered on 9.0 ml 30% w/w sucrose in polycarbonate bottles—sharp interface. The sucrose is sterile and endotoxin negative as determined by a quantitative Limulus assay.

Sample size: 4–5 ml cleared/filtered lysate

Centrifugation: 0°–4° C.; slow acceleration; 30,000 rpm; 120 minutes at speed. The time at speed (+or −) is adjusted to maximize yield and minimize contamination. This depends on the volume of lysate layered. Brake off occurs at 1000 rpm. (Not less than 500 rpm.) See manufacturers' instructions for brake off recommendations for specific centrifuge/rotor combinations.

14 Beckman Rotor:

gradient: 100 ml 25% w/w sucrose cushion in polycarbonate bottles. The sucrose is sterile and endotoxin negative as determined by a quantitative Limulus assay.

Sample size: 100 ml cleared/filtered lysate.

Centrifugation: 0°–4° C.; slow acceleration; 14,000 rpm; 12 hours at speed; brake off at 500 rpm during deceleration

10 Beckman Rotor:

gradient: 200 ml 25% w/w sucrose cushion in polycarbonate bottles. The sucrose is sterile and endotoxin negative as determined by a quantitative Limulus assay.

Sample Size: 200 ml cleared/filtered lysate.

Centrifugation: 0°–4° C.; slow acceleration; 10,000 rpm; 23 hours at speed; brake off at 500 rpm during deceleration.

The second centrifugation procedure allows the isolation, via pelleting, of the specifically sized membrane vesicle fraction and the residual ribosome fraction, leaving smaller fractions such as DNA fragments, RNA fragments, protein fragments, cell wall fragments, and membrane fragments, in the upper portions of the discontinuous gradient. The specific centrifugation time in these rotors is such that the final product is not significantly contaminated by unwanted cellular components. If the centrifuge times cannot be changed to reduce the amount of the above contaminates, the following wash procedure can be used:

For example, for the #30 Beckman rotor:

a. The pellets (from the #30 Beckman rotor or equivalent rotor, see above) are resuspended with 10 ml of suitable buffer per 12 tubes. The resuspended pellets are transferred to a sterile, non-pyrogenic microclean container. The centrifuge tubes are then rinsed with 2 ml of suitable buffer per 10 tubes. The rinse is then combined with the resuspended pellets in the appropriate container. The solution is mixed by repeatedly pipetting (10 times with a 10 ml syringe) or by swirling for a few seconds.

b. 5 ml of the resuspended pellets is pipetted into a sterile, non-pyrogenic #30 rotor polycarbonate centrifuge tube containing 15 ml of suitable buffer.

c. The tubes are centrifuged for 25 to 40 minutes normal acceleration and brake on.

Other types of centrifuges and rotors may be utilized as long as the methodology is equivalent (e.g., 50.2 Ti Beckman Rotor provides a shorter run time utilizing the same size gradients). Appropriate linear gradients may be utilized instead of the discontinuous gradient.

The pelleted fraction isolated in accordance with the foregoing described procedure is washed and then suspended in one of the suitable suspending liquids or buffers described above and filter sterilized with a suitable 0.45 or 0.22 micron filter. The suspending liquid may be of any appropriate pharmaceutical or preferably reagent quality devoid of fractions which might contribute to the precipitation, degradation, aggregation or functional inhibition of the suspended fraction.

Product quantitation is based on nucleic acid content which is determined by the following formulas:

$E_{260} = 0.0373 - 0.0079 (A_{260}/A_{280})$

Micrograms Nucleic Acid $= A_{260}/E_{260}$

A 0.05 ml sample of the resuspended product concentrate is diluted in the appropriate resuspending buffer so that the $A_{260}$ is between 0.4 and 0.5 for standardization purposes. The absorbances at 280 nM, 260 nM, 225 nM and 215 nM are then determined using the suspending buffer as the blank. Once the nucleic acid content has been determined, the product is diluted to a final concentration of 1.0 mg nucleic acid per 0.5 ml buffer. The protein content of the product may be approximated by using the formula:

micrograms protein/ml $= 144(A_{215} - A_{225})$.

Average product yield using centrifugation is 1.0–1.2 nucleic acid mg per 0 ml cleared lysate. The $A_{260}/A_{280}$ absorbance ratio mean is 1.7626 with a standard deviation of 0.0626. The mean $E_{260}$ is 0.0232 with a standard deviation of 0.0007.

The reason for the high functional efficacy (described below) of product having vesicles of this size is at present not completely understood. Nevertheless, it is believed that the size of the membrane vesicles as specified, namely a mean diameter of at least 180 nm, and substantially a minimum size of about 110 nm, is significant.[15/]

The preparation of the invention has tolerable levels of biologically active endotoxins and cell wall fractions, clearly reducing toxicity problems. For example, the invention does not induce cutaneous necrosis/ulceration or death in four day old mice as shown below in Table 1. In this study, four day old C57Bl/6 mice were injected with the invention in the nuchal (neck) region and observed for the development of necrosis and/or death. In addition, these animals demonstrated normal weight gain, another indicator of the absence of toxic contaminants.

TABLE 1

| | DERMONECROTIC TEST | | | | |
|---|---|---|---|---|---|
| | Invention | Necrosis/Death | | | |
| No. Animals | Dosage | 18 hr. | 24 hr. | 48 hr. | 96 hr. |
| 4 | 10 µg | 0/0 | 0/0 | 0/0 | 0/0 |
| 7 | 100 µg | 0/0 | 0/0 | 0/0 | 0/0 |
| 6 | 200 µg | 0/0 | 0/0 | 0/0 | 0/0 |

Histamine hypersensitivty testing in 8 week old CFW mice also evidenced an absence of toxicity due to endotoxin.

TABLE 2

HISTAMINE HYPERSENSITIVITY TEST

| | ROUTE | D/T[a] |
|---|---|---|
| A. ENDOTOXIN DOSAGE (micrograms) | | |
| *E. coli* (PHENOL, SIGMA) | | |
| 0.5 | i.p. | 4/6 |
| *E. coli* (TCA, SIGMA) | | |
| 0.5 | i.p. | 3/6 |
| B. INVENTION DOSAGE (micrograms) | | |
| 100 | i.p. | 0/6 |
| 200 | i.p. | 0/6 |
| 600 | i.p. | 0/6 |
| 2000 | i.p. | 0/7 |

[a]Deaths per total number of mice treated following i.p. challenge with 0.5 mg histamine diphosphate (Sigma) 90 minutes after administration. Endotoxin (0.5 micrograms) administered i.p. results in 50% death following histamine challenge[7]. Mice, rats and guinea pigs typically demonstrate hypothermic responses following the administration of endotoxin or infectious challenge whereas they develop hyperthermia (1–2° C.) following the administration of the invention.

Furthermore, single or repeated injections in mice, rats, quinea pigs and humans (more than one hundred subjects) has not resulted in anergy, pruritis, DIC (disseminated intervascular coagulation), adjuvant arthritis, anaphylaxis (hypersensitivity), elevation of hepatic enzymes, or necrosis or ulceration of local injection sites, over a dosage range of 5 micrograms to 10 milligrams (administered one to three times weekly in human subjects). The maximum total dose in one week has not exceeded 12 milligrams. Bilateral hemorrhagic necrosis of the kidneys has not occurred when administered intravenously to rabbits.

The membrane vesicles in the product of the invention appear to be readily endocytosed by monocytes and macrophages as observed with phase-contrast microscopy. It is known that endocytosis results in cell membrane turnover and that membrane cycling in the monocyte-macrophage cell line activates these cells.

The cells of the monocyte-macrophage cell line are artificially broken up into several functional categories with each representing a progressively more differentiated cell. These categories (terminology may vary) are: monocyte, normal or resident macrophage, stimulated macrophage, activated non tumorcidal macrophage, and activated tumorcidal macrophage. The more differentiated the cell, the less refractory it is to various types of stimulation but the more restricted it may potentially become in effector functions. Conversely, in advanced disease and chronic disease states, the monocyte-macrophage cell line becomes progressively more refractory to stimulation as does the immune system in general. Of these stages, only the activated tumorcidal macrophage has been demonstrated to be directly cytotoxic to tumor cells.

More specifically, monocyte-macrophage product endocytosis has been noted in connection with murine cells. Normal monocytes and resident macrophages were harvested from healthy adult C57Bl mice, without any prior manipulative procedures and without heparin, from the peritoneal cavity. The initial adherent cell population consisted of over 90% rounded cells with the remaining having the typical morphology of macrophages. Round cell populations consisted of monocytes and large numbers of cells having the appearance of medium sized lymphocytes. All cells endocytosed product and were therefore members of the monocyte-macrophage cell line.

Within minutes following the in vitro addition of the product of the invention to a purified virgin monocyte-resident macrophage (rounded cell) population, numerous minute vesicles, which increase in size and number with time, began appearing just beneath the cell membranes. Phagocytic activity varied in direct proportion to the concentration of the invention added. Autophagocytic death preceded by extreme vacuolization with maintenance of a rounded cell morphology occurred when the invention concentration exceeded 50 micrograms per 3 ml media/$10^5$ cells. Neither phagocytic activity nor cellular activation was observed following the addition of endotoxin or BCG cell walls at various concentrations to identical cell populations. B16 melanoma and kidney epithelial cells did not exhibit phagocytic activity in the presence of the invention or in the presence of endotoxin or BCG cell wall products. There is a possibility that a receptor specific for a component of the vesicles and/or ribosomes of the invention exists which would account for the apparent rapid internalization of the invention by the monocyte-resident macrophages. Other explanations involving nonspecific physical and/or chemical interactions (such as relative hydrophobicity) are also possible.

Table 3, set out below, summarizes the results of a monocyte-resident macrophage cytotoxicity study wherein the invention was administered in vitro, using concentrations of 0 to 100 micrograms at 5 microgram intervals to 25 cm[2] flasks containing $10^5$ B16 melanoma cells as targets and mouse peritoneal monoctyes-resident macrophages as effector cells. The effector to target ratios are indicated in the left-hand column. The cells were fixed in 95% ethanol and stained with Mayer's hematoxylin 96 hours after initiation of the assay. Those results indicated by a plus sign mean that macroscopic growth was readily visible at 80%–100% confluence. A negative sign indicates that no visible macroscopic growth was present with a significantly reduced or absent target cell population confirmed microscopically.

TABLE 3

TUMOR CYTOTOXICITY ASSAY
VISIBLE (CONFLUENT) GROWTH AT 96 HOURS
AT PRODUCT CONCENTRATION (micrograms)

| E/T RATIO | 0 | 3 | 5 | 10 | 15 | 20 | 25 | 30 | 35 | 40 | 45 | 50 | 55 | 60 | 65 | 70–100 |
|---|---|---|---|---|---|---|---|---|---|---|---|---|---|---|---|---|
| 2:1 | + | + | − | + | − | + | + | + | + | + | + | − | + | + | + | + |
| 1:1 | + | + | − | + | − | + | + | + | + | + | + | − | + | + | + | + |
| 1:2 | + | + | − | + | − | + | + | + | + | + | + | − | + | + | + | + |
| 1:4 | + | + | + | + | + | + | + | + | + | + | + | + | + | + | + | + |

From the above table, it may be seen that very specific concentrations (5, 15, and 50 micrograms) of the invention directly induce the differentiation of peritoneal monocyte-resident macrophages to a tumor cytotoxic state. High levels of cytotoxicity are achieved at effector-target ratios of 2:1 or less. The tumor cytocidal effects observed were extreme vacuolization, cellular contraction and/or increase in phase density, and were observed within as little as eight hours following the addition of the effective concentrations of the invention.

Previously published studies show that activated non-tumorcidal macrophages require 18 hours exposure to lymphokines before they will kill target cells with monocytes and resident macrophages not responding. The cytotoxic activity induced in monocyte-resident macrophages by the product of the invention is very rapid and unique. The fact that the cultures were incubated for four days prior to termination demonstrates the rapid and efficient induction of effector cell function and long term target cell control as a result of the administration of the invention.

The ability of the product of the invention to alter the levels of various white blood count (WBC) and neutrophil levels is shown in Table 4. Table 4 indicates the WBC and neutrophil levels for a series of terminally ill human patients taken prior to and subsequent to administration of the invention. Dosage levels are indicated. The product was administered once a week for three weeks. It may be seen from the examples in Table 4 that the specified treatment using the invention significantly increases the white blood cell count and neutrophils. It is noted that the alteration of white blood count does not necessarily increase for all dosages nor for all patients. (It does not decrease.) However, certain patients, as shown in Table 4, respond to administration of the invention by significant increase in white blood cell count and neutrophils.

TABLE 4

| Patient No. | Invention Dosage (mg) | WBC × 1000 Before | WBC × 1000 24 h. After | Neutrophils (% WBC) Before | Neutrophils (% WBC) 24 h. After |
|---|---|---|---|---|---|
| D59261 | 1.0 | 18 | 27 | 88 | 92 |
| D25940 | 1.0 | 3.8 | 6.2 | 58 | 70 |
| D78252 | 1.5 | 8 | 10.5 | 67 | 82 |
| D45851 | 1.5 | 8.6 | 13.6 | 77 | 90 |
|  | 3.0 | 13.3 | 22.7 | 90 | 92 |
| D80822 | 2.0 | 6.7 | 7.6 | 59 | 74 |
|  | 3.0 | 6.1 | 9.6 | 59 | 75 |
| D82088 | 4.0 | 3.2 | 9.4 | 70.3 | 93 |
|  | 6.0 | 3.5 | 6.3 | 56 | 85 |
| D90607 | 6.0 | 8.0 | 9.6 | 72 | 84 |

Normal Ranges
WBC 7.8 ± 3 × 1000
Neutrophils 40-70%

Patients with low WBC counts prior to therapy enter normal range 24 hours after therapy. Administration of the invention also results in increases in human peripheral blood mononuclear counts (natural killer cells, cytotoxic T-cells and/or monocytes) and does not result in thrombocytopenia (data not shown). The product of the invention therefore does not have a cytostatic effect on bone marrow.

Proper immune function requires the coordinate cooperation of several cell types and the sequential production and release of numerous cellular products. It is known that the cells of the monocyte-macrophage cell line are central in this process in that optimal antibody responses (B-cell function), cell mediated immunity (T-cell function), and possibly natural killer (NK) cell activity, do not occur in their absence. Although it is possible to elucidate various cooperative cellular pathways in tissue culture, it is not possible to determine the multitude of pathways and the operative control mechanisms in the human patient. Since, in the patient, the various specific and/or nonspecific immune effector mechanisms occurring are essentially unknown, an agent selected to potentiate/modify immune function should augment any ongoing responses or, in the absence of responses, lower the system response threshold, thus allowing recognition, activation and selection of the appropriate effector functions. The ideal activating agent should not induce immune deviating, anergic or aberrant hypersensitivity responses directed to itself or cross-reacting entities, or promote or direct the selection of a specific singular effector pathway. The product of the invention fulfills these requirements as none of these phenomena have been observed at significant levels during clinical trials.

FIG. 2 illustrates the ability of the biologic response modifier of the invention to stimulate human natural killer cells in a manner comparable to that of leukocyte interferon. The in vitro assay illustrates the degree of lysis of target cells (measured in terms of the release of radioactive chromium from target cells) by action of human natural killer cells for various dosage levels of the invention and interferon, shown in the respective graphs. The dosage level codes are given below each graph, with the zero dosage level representing the background or leakage level of chromium release from target cells.

The assays were conducted in accordance with those described in the literature.[8/ 9/] Human K562 cells of the myeloid tumor line were labeled with radioactive sodium chromate and serve as the target cells. The effector cells utilized were non-depleted human peripheral blood mononuclear cells. Killing is calculated by the following formula:

$$\% \text{ release} = \frac{\text{Experimental release} - (\text{minus}) \text{ Control release}}{\text{Maximum release} - (\text{minus}) \text{ Control release}} \times 100$$

Experimental release is the counts per minute (CPM) of radioactivity in the presence of product and effector plus target cells, and control release is the counts per minute obtained with the use of effector plus target cells only. Maximum release is obtained by incubating an aliquot of target cells in saponin, a detergent.

The results in this example indicate that, although not quite as high as interferon for relatively lower effector to target cell ratios, nevertheless the induction of human natural killer cell cytotoxicity in the presence of monocytes definitely occurs at a significant level comparable to that of interferon. Statistical analysis of over 30 product lots, as illustrated in FIG. 2, demonstrate that the invention is equivalent to or better than leukocyte interferon in the induction of NK cell cytotoxicity, especially for effector to target cell ratios exceeding 25:1. Product NK cell cytotoxicity parallels interferon induced cytotoxicity and depends upon a number of variables including the blood donor's age, sex, method of cell storage, and ratio of cell types present.

Referring now to FIG. 3, the bacteriocidal properties of the biologic response modifier of the invention are illustrated. The graph in FIG. 3 depicts, on the ordinate, the log number of *Listeria monocytogenes* in mouse peritoneal cells. The abscissa represents time, in hours. *Listeria monocytogenes* is a bacterium which causes an acute meningitis in humans with or without associated septicemia. The assay depicted in FIG. 3 is a standard assay for bacteriocidal activity. The control is proteose peptone which is known to elicit bacteriocidal macrophages but which is not tolerated by humans. The assay is described in Cruprinski, C. J., Henson, P. M., and Campbell, P. A., 1984, *J. Leukocyte Biol.* 35:193.

The lines on the graph indicate the change in the number of bacteria in culture over three hours when they are exposed to cells harvested from the peritoneal cavities of mice at varying times and for several different preconditioning steps as follows:

A. no peritoneal cells—bacterial growth control;
B. intraperitoneal injection of proteose peptone 14 days prior to harvesting;
C. intraperitoneal injection of invention 14 days prior to harvesting;
D. intraperitoneal injection of invention 7 days prior to harvesting;
E. intraperitoneal injection of invention 1 day prior to harvesting; and
F. intraperitoneal injection of proteose peptone 1 day prior to harvesting.

As may be seen from FIG. 3, the upper lines, representing the controls, indicate that the cultures grew steadily. The situation wherein the cells were harvested from the mice after 0.2 milligrams of the product of the invention had been injected intraperitonealy show growth declines at varying slopes depending upon the time of injection before harvesting, substantially matching the proteose peptone control in the 1-day situation. These data show that the bacteriocidal inducing activity of the product remains high even 14 days after a single injection. Thus, the prolonged effect of the biologic response modifier of the invention in inducing macrophages with pronounced bacteriocidal activity demonstrates its usefulness as a therapeutic agent for bacterial infections.

The ability of the biologic response modifier of the invention to modulate the activity of antibody dependent cellular cytotoxicity (ADCC) is shown in FIG. 4. Procedures followed have been described in the literature.[10][11] In this assay, human peripheral blood monocytes are used as the effector cells at the specified effector-target ratios. Target cells were chromium labeled murine YAC cells and the antibody utilized was rabbit anti-mouse cells.

It may be seen from FIG. 4 that the killing level, at least for relatively high effector to target cell ratios, is higher for the product of the invention than for interferon at product dosage levels of 15 and under micrograms per milliliter, but appeared to be in the background level at 20 micrograms per milliliter (a concentration which results in autophagocytic death of the monocyte population in this assay).

The ability of the invention to stimulate the release of interleukin 1 (IL-1) is illustrated in FIG. 5. Assay procedures followed have been described in the literature.[12][13] Peripheral blood mononuclear cells were prepared from blood drawn from human subjects to be tested. The cells were incubated in various concentrations of the product of the invention. After a specified incubation period aliquots of the culture medium were harvested and tested in a blastogenesis assay at various dilutions. Blastogenesis was determined by the counts per minute of radioactive (tritiated) thymidine taken up by $10^6$ murine thymocytes following 72 hours incubation in the harvested culture supernatants. In FIG. 5, the background level is indicated by the solid circles. It may be seen that, except for the lowest dosage of 1 microgram per milliliter, significant stimulation of IL-1 release occurred. The therapeutic benefits of IL-1 release have been documented in the literature.[14]

That the cytotoxic effect against K562 targets is due to natural killer cells and is not affected by B or T-cells is illustrated in FIG. 6. Human peripheral blood mononuclear cells were used for the effector population at the effector-target ratios specified. It may be seen that, without the invention or in the absence of natural killer cells, the background or leakage level is below 20% chromium release. With a non-depleted cell population, administration of the invention results in clear stimulation of natural killer cell cytotoxicity. Removal of B or T-cells from the population with specific monoclonal antibodies does not significantly affect the level of cytotoxicity. Removal of NK cells with monoclonal antibodies is shown to eliminate the cytotoxic effect. Removal of monocytes with monoclonal antibodies (not shown) also results in loss of NK cytotoxicity, suggesting that the NK cell is activated by the monocyte-macrophage population.

Referring now to FIG. 7, a graph of the results of an in vivo study on rat prostatic squamous cell carcinoma (rapid growth tumors) is illustrated. It may be seen that the administration of the invention induced the regression of large, established, rapidly growing carcinomas in rats. All non-treated tumor bearing controls had expired within a 14 month period whereas all treated animals were alive and 4 out of 6 animals totally regressed their tumors. In conducting these studies, it was discovered that a 1 milligram weekly paralesional injection was effective whereas a 2 milligram weekly injection was not. The specific carcinoma treated was the Dunning tumor subline R3327A, a non-hormonally dependent, moderate-fast growth rate tumor which is metastatic in advanced disease. The tumor host was Copenhagen X Fisher $F_1$. This tumor system is a model for the national Prostatic Cancer Group. Implantation was in the left flank. Mean tumor volume at first treatment was 681 cubic millimeters.

Referring now to FIG. 8, a study of the invention in connection with slow growth rat prostatic carcinoma is illustrated. The tumor hosts were Copenhagen X Fisher $F_1$. This represents another tumor model for the National Prostatic Cancer Group. Implant was in the left flank. Treatment consisted of 2 milligram paralesional injections every seven days. The mean tumor volume at initiation of treatment was 1138.8 (>2 cm$^3$) cubic millimeters. The specific carcinoma was Dunning tumor subline R3327H, which is a well differentiated adenocarcinoma, demonstrating a very slow growth rate.

In FIG. 8, it may be noted that the invention induced stabilization/regression of large established slow growing carcinomas in rats. All control, non-treated, tumor bearing animals demonstrated progressive disease, death and weight loss whereas all treated animals showed disease stabilization, progressive slow regressions (indicated by pathology), normal weight and no deaths. In this case, whereas the 2 milligram weekly paralesional injection was effective, a 1.0 milligram weekly paralesional injection was not. The above two tumor systems demonstrate the expected effective dosage variance with different tumors.

Referring now to FIG. 9, a study of bilateral rat prostatic adenocarcinoma tumors is shown. Comparisons to a control group are made with hosts receiving orchiectomy, orchiectomy plus dosage with the invention, steroid plus dosage with the invention, and dosage with the invention only. Comparisons are with left flank and right flank tumors.

In FIG. 9, it may be noted that the invention induced the regression of very large (total greater than 5 cubic centimeters) moderately fast growing adenocarcinomas. Treated animals receiVed weekly 1 milligram paralesional injections at the left flank tumor site only. The data demonstrate the systemic effect of therapy (contralateral untreated lesions regressing) utilizing the invention and lack of inhibition of the biologic response modifier effect by the steroid dexamethasone. Dexamethasone has not been observed to inhibit the hyperthermic response in human tumor bearing patients.

In vivo human clinical studies have been conducted utilizing the invention pursuant to regulations and procedures for Phase I and Phase II testing promulgated by the Food and Drug Administration of the United States. Phase I studies were for the purpose of determining the toxicity, if any, of the invention. Pursuant to Phase I tests, the patients studied were in an advanced state of disease, were considered terminal, and had failed all previous therapy. These patients received three or six treatments at each of the indicated dosage levels administered every 7 days subcutaneously at a site remote from the site of the tumor. The toxicity trials indicated no significant toxicity problems and that the product is well tolerated in humans.

At the same time, moreover, in 46% of the cases a therapeutic effect was noted. The Phase I results are set forth in the following table.

TABLE 5

PATIENT RESPONSE SUMMARY

| Patient No. | Dosage (mg) | Diagnosis | Response |
|---|---|---|---|
| D44937P | .25, .50, 1.0 | Pulmonary CA | stable |
| D06277 | .25 | Prostatic CA | minor |
| D32770 | .25 | Pulmonary CA | none |
| D01088 | .50 | Breast CA | stable |
| D15546 | .50 | Colon/Liver | none |
| D59261 | 1.0, 2.0 | Lymphoma (HL) | minor |
| D25940 | 1.0 | Germ Cell | none |
| D78252 | 1.5 | Colon/Liver | none |
| D45851 | 1.5, 3.0, 5.0, 6.0 | Adeno CA rectum/abd | minor |
| D180849 | 2.0, 3.0 | Breast CA | none |
| D80822 | 2.0, 3.0 | Lymphoma (LHL) | none |
| D81828 | 2.5, 8.0 | Lymphoma (NHL) | partial |
| D62984 | 2.5, 4.0 | Lymphoma (HL) | stable |
| D82088 | 2.5, 4.0, 6.0 | Glioblastoma | minor |
| D76339 | 4.0, 6.0 | Pancreatic | stable |
| D82568 | 4.0 | Kaposi Sarcoma | stable |
| C03343 | 5.0, 8.0 | Renal cell | stable |
| D87354 | 5.0, 1.5 | Nodular lymphoma | partial |
| D90607 | 6.0 | Adeno CA lung | none |
| D91834 | 6.0 | Melanoma | none |
| A039585 | 0.25 | Renal cell | stable |
| A768642 | .25, .5, 1.0, 2.0 | Colon/liver | stable |
| A661981 | 0.5 | Pulmonary CA, adeno | stable |
| A078379 | 0.5 | Parotid CA | minor |
| A017231 | 0.25 | Colon CA | none |
| A055001 | 1.0 | Pulmonary | stable |
| A666522 | 1.0 | Pulmonary CA large cell | none |
| A403927 | 1.0 | Pulmonary CA squamous | none |
| A032896 | 1.5 | Adeno CA, neck | partial |
| A708029 | 1.5 | Bronchioalveolar | stable |
| A044130 | 1.5 | Pulmonary CA squamous | stable |

TABLE 5-continued

PATIENT RESPONSE SUMMARY

| Patient No. | Dosage (mg) | Diagnosis | Response |
|---|---|---|---|
| A223211 | 2.0 | Pulmonary CA | stable |
| D47379 | 8.0 | prostate | none |
| D88652 | 5.0 | colon | none |
| D93503 | 8.0 | colon | stable |
| D94245 | 8.0 | NH lymphoma | minor |
| D86141 | 8.0 | colon | none |
| D96464 | 8.0 | melanoma | none |
| D94257 | 10.0 | Gallbladder | none |
| D97735 | 10.0 | colon | none |
| E01514 | 10.0 | NSC lung | stable |
| D98520 | 10.0 | colon | none |
| E01401 | 10.0 | sarcoma | none |
| D66399 | 1.0 | mediastinal mass | none |
| 6134 | 2.0 | lung | stable |
| 3374 | 2.0 | lung/prostate unk. primary | stable |
| 4277 | 4.0, 6.0 | lung | stable |
| 5079 | 3.0 | stomach | none |
| 0421 | 4.0 | histiocytoma | partial |
| 6918 | 6.0 | gallbladder | none |
| 2688 | 8.0 | tongue | none |
| 8708 | 8.0 | colon | none |
| 9222 | 8.0 | prostate | none |
| E07942 | 2.0 | colon | none |
| E13150 | 4.0 | small cell lung | stable |
| E14356 | 4.0 | neck | none |
| E15735 | 4.0 | rectal | none |
| D69174 | 3.0, 4.0 | colon | none |
| E11927 | 4.0 | NSC lung | none |
| E14983 | 4.0 | Kaposi sarcoma | none |
| D70727 | 3.0, 4.0 | lung | stable |
| E07876 | 2.0, 3.0 | renal | stable |
| E04693 | 1.0, 2.0 | breast | minor |
| E10311 | 3.0 | larynx | none |
| E09265 | 3.0 | renal | none |
| D44296 | 0.5 | colon | none |
| D81828 | 2.0 | NH lymphoma | none |
| E07727 | 1.0, 3.0 | breast | none |
| E03741 | 0.5 | colon | none |
| E05487 | 2.0 | parotid | none |
| E03083 | 0.5, 1.0 | endometrium | stable |
| E04545 | 1.0 | mixed lymphoma | none |
| E05195 | 2.0 | thymoma | minor | partial = 50% or greater reduction of disease
minor = more than 25% but less than 50% reduction of disease
stable = disease not progressing
none = no response
The above data show a 46% response rate in advanced disease, terminal patients who have all failed previous therapy.

The specific dosage level and treatment interval selected for therapy on a human patient will often vary from patient to patient. The factors which influence dosage level and treatment interval include the patient's overall immune system response characteristics, the particular type and extent of disease, the overall health of the patient, the location of the disease, etc. This is essentially no different from other biologic response modifiers and the most beneficial dosage schedules may be determined in accordance with techniques used in connection with such other biologic response modifiers, and with pharmaceuticals generally.

The fact that efficacy may be highly significant in certain diseases as compared with other available treatments is evidenced from the data in Table 6, below, relating to the treatment of brain tumor, for example, glioblastoma. The data in Table 6 indicate that for six cases of brain tumors, three showed decrease in tumor size even with limited treatment. This clearly indicates that the biologic response modifier of the invention demonstrates an efficacy with respect to this particular tumor type.

TABLE 6

| PATIENT RESPONSE SUMMARY - BRAIN TUMORS | | | |
|---|---|---|---|
| Patient No. | Dose (mg) | Diagnosis | Response |
| D82088 | 2.5, 4.0, 6.0 | Brain | minor |
| E11928 | 1.0 | Brain | partial |
| E34415 | 1.0, 3.0 | Brain | progression |
| E37376 | 1.0, 3.0 | Brain | significant functional improvement |
| RT | 1.0, 3.0 | Brain | progression |
| DR | 1.0, 3.0 | Brain | partial |

The membrane vesicles and ribosomes used in the invention are readily biodegradable. A particularly noteworthy advantage of the degradation phenomenon is that the particulate populations of the product of the invention stay intact in the biological system only for a short period of time sufficient to activate the immune reaction, and thereafter rapidly degrade. Hence, the development of severe, chronic pathophysiologic reactions, as a result of chronic immune activation, are avoided. Degradation is due to the presence of various enzymes (e.g., RNases proteases, lipases) in various types of cells (e.g., monocytes, macrophages, neutrophiles) and tissue fluids (e.g., blood, lymph). This degradation is more rapid at elevated temperatures (e.g., body temperature, 37° C.) and becomes progressively slower as the temperature is reduced. At 37° C. and 95% serum concentration, the product is degraded (in vitro) in less than about two minutes as determined by particle size analysis. The rate of degradation is dependent upon the enzyme concentration and temperature.

Referring now to FIG. 10, the human in vivo induction of killer cell cytotoxicity against three different tumor targets is depicted. For most individuals, peripheral blood mononuclear cells will kill K562 tumor target cells in vitro to some extent. However, peripheral blood mononuclear cells typically will not kill the Raji and Colon 38 tumor cell lines. Treatment of patients by in vivo administration of various biologic response modifiers, including interleukin II (IL-2) has not been perceived to change the level of killing with respect to the latter two target cells. Only in vitro treatment of the peripheral blood mononuclear cells with certain biologic response modifiers, including IL-2, induces these cells to kill types of tumor target cells other than K562. However, it has been discovered that the biologic response modifier of the invention is capable of altering the peripheral blood mononuclear cell's capability to kill such tumor targets following in vivo treatment. This suggests LAK cell (cytotoxic T-cell) induction occurs following administration of the invention.

FIG. 10 is representative of the in vitro measurement of killer cell cytotoxicity in peripheral blood mononuclear cells obtained from patients 24 hours after treatment with the biologic response modifier of the invention. It may be seen that significant killing results against all three types of tumor targets. The data demonstrate significant in vivo activation of the patient's killer cells. Examination of the effector cell population via specific cell markers shows the presence of activated monocytes, natural killer cells and LAK cells. The increases in natural killer cells observed in treated patients (previously discussed) and the presence of activated natural killer cells in this assay demonstrate endogenous production of interferon in these patients following treatment with the product of the invention. In addition, the presence of activated cytotoxic "T-cells" (LAK cells) demonstrates that treatment with the invention results in endogenous IL-2 production. Another unique property of the produce of the invention is that the in vivo activated killer cell populations can be maintained in vitro with very low (2U IL-2/ml) concentrations of IL-2. This contrasts with the high concentrations of IL-2 (500–1000U IL-2/ml) necessary to maintain in vitro IL-2 activated killer cells (LAK cells).

The peripheral blood mononuclear cells used were obtained from whole blood collected from patients 24 hours after injection with the biologic response modifier of the invention. Injections were subcutaneous and varied from one to four milligrams per dose, given 3 times per week. The assays were performed prior to and 24 hours after injection. The level of cytotoxicity obtained with in vivo activated cells compares favorably with the activity of in vitro lymphokine (IL-2) activated killer cells obtained after culturing human peripheral blood mononuclear cells with IL-2.

The superiority of membrane vesicles and ribosomes derived from organisms of the claimed type, such as *Serratia marcescens*, as compared with other sources is suggested by the data obtained from comparative natural killer cell assays (FIGS. 11 and 12). Product was prepared by the method described above from the indicated organisms. The vesicles prepared from each of these organisms were within the physical and chemical parameters designated above.

The fact that the source of a given bacterial product influences the type and/or degree of biologic activity is not new to this field. Different strains of BCG demonstrate specific levels of immune activation in animal models and clinically. Ribosomal vaccines (previously discussed) cause differential activation of the immune system depending upon the source organism; and the superiority of polyribosomes obtained from Serratia as compared with other sources has been suggested.[6/] In the cited publication, administration of buffer alone and bacterial polysomes derived from other bacterial species (*Escherichia coli, Streptococcus pneumoniae, Mycobacterium bovis*, [BCG], *Mycobacterium smegmatis*, and *Propionibacterium acnes*) were little better than a control group of the mice which received no treatment (tumor appearance and death within 60 days). On the other hand, polysomes obtained from *Serratia marcenscens*, at certain dosages, demonstrated absence of tumor development in 60% or more of the animals and suppression in the development of tumors in the remaining animals.

Because the biologic response modifier of the invention is obtained from a microorganism that is not a member of the microflora of the patient, is not associated with infectious disease in normal individuals, and because the microorganism's common bacterial antigen does not cross-react or is poorly cross-reactive with organisms making up the normal microflora, inappropriate immune responses are avoided. Such responses include, for example, immune deviation and the phenomenon of original antigenic sin which is commonly observed with currently developed immunopotentiators (e.g., BCG, *C. parvum*, cell wall fractions). Probably for these reasons, polyribosome aggregates prepared from *E. coli, M. smegmatis* and *Streptococcus pneumoniae* are very poor sources for biological responses, whereas *S. marcescens*, which is not part of and does not readily crossreact with host microflora, is an excellent source of the biologic response modifier.

It is to be noted that there are other microorganisms which are suitable as a source for the membrane vesicles and ribosomes utilized in the invention. The basic characteristics of such microorganisms must be that the microorganism is not a member of the microflora of the patient. Moreover, the microorganism's common bacterial antigen must not react or at least must be poorly cross-reactive with organisms making up the normal microflora. Thus, the organism should not be one which evokes an immune deviating response. The organism must be one which does not or rarely causes disease in humans. Finally, the source microorganism must be one in which the cellular membrane forms vesicles in the appropriate size range.

Examples of suitable microorganism sources other than *Serratia marcescens* are: *Erwinia chrysanthemi* (Pectobacterium) ATCC 14092; and, to a lesser extent, *Enterobacter aerogenes* ATCC E13048. Preparations from the above strains exhibit activity of the type described above in connection with preparations from *S. marcescens*. More particularly, FIG. 11 shows that *E. aerogenes* demonstrates significantly greater effectiveness than *Pseudomonas, E. coli,* and *E. cloacae,* though less than alpha interferon at specific dosage levels. Similarly, FIG. 12 compares *E. chrysanthemi* (effective) with Flavobacterium (not effective) and interferon. Other microorganisms may be used as sources and processed as above to produce ribosomes and vesicles of the size specified. Using the previously described in vitro assays, their effectiveness may be readily assessed to determine whether or not they are useful as a biologic response modifier.

Because the biologic response modifier of the invention is free of viable cells and dead cells, and has tolerables levels of cell wall and membrane fragments and biologically active endotoxin, the effects of those components, which are known to be highly toxic or which can result in chronic inflammatory situations e.g., adjuvant arthritis, granulomas, ulcerations, are minimized or eliminated.

The advantages of the biologic response modifier of the invention are numerous. By activating cells of the monocyte-macrophage cell line, the cellular cooperation necessary for optimal immune function is promoted. Activation of early differentiated cells of the monocyte-macrophage cell line (monocyte, normal/resident macrophage) promotes multiple effector functions. The composition of the invention has thus far demonstrated induction of multiple types of effector functions dependent upon the condition of the assay or disease host parameters.

Various modifications of the invention, in addition to those shown and described herein, will become apparent to those skilled in the art from the teaching of this specification. Such modifications are intended to fall within the scope of the appended claims.

FOOTNOTES

1/Millman, et al., *Proc. Soc. Exp. Biol. Med.,* 147:765-768, 1974, *Infect. Immun.,* 14:929-14 933, 1976.

2/Thomas, D. W., and Weiss, E., *Infect. Immun.,* 6:355-363, 1972. 3/Klun, D. L. and Youmans, G. P., *RES J. Recticuloendo Thel. Soc.,* 13:263-274, 1973.

4/Smith, R. A., and Bigley, N. J., *Infec. Immun.,* 6:384-389, 1972.

5/Swendsen, C. L., and Johnson, W., *Infec. Immun.,* 14:345-354, 1976.

6/*Cancer Research,* 40:1501-1505, 1980.

7/Bergman, R. K., et al., *Infection and Immunity,* 18:352-355, 1977.

8/West, W. H., Cannon, G. B., Kay, H. D., Bonnar, G. D. and Herberman, R. B. (1977) Natural cytotoxic reactivity of human lymphocytes against a myeloid cell line: characterization of effector cells. *J. Immunology* 118:355.

9/deLandazuri, M. O., Silva, A., Alvarez, J. and Herberman, R. B. (1979) Evidence that natural cytotoxicity and antibody-dependent cellular cytotoxicity are mediated in humans by the same effector cell populations. *J. Immunology* 123:252.

10/Fuson, E. W., Whitten, H. D., Ayers, R. D. and Lamon, E. W. (1978) Antibody-dependent cell-mediated cytotoxicity by human lymphocytes. I. comparison of Igm- and IgG-induced cytotoxicity. *J. Immunology* 120:1726.

11/Kay, H. D., Bonnar, W. H., West, W. H. and Heberman, R. B. (1977) A functional comparison of human Fc-receptor-bearing lymphocytes active in natural cytotoxicity and antibody-dependent cellular cytotoxicity. *J. Immunology* 123:252.

12/Conlon, P. J. (1983) A rapid bilogic assay for the detection of Interleukin 1. *J. Immunology* 131:1280.
13/Wood, D. D., Bayne, E. K., Goldring, M. B., Gowen, M., Hamerman, D., Humes, J. L., Ihrie, E. J., Lipsky, P. E. and Staruch, M. J. (1985) The four biochemically distinct species of human Interleukin 1 all exhibit similar biologic activities. *J. Immunology* 134:895. 14/Dinarello, C. A., 1984, *New Eng. J. of Med.,* 311:1413-1418. 15/Kreuter, J. and Haenzel, I., 1978, *Infec. and Immun.* 19:667-675.

What is claimed is:

1. A biologic response modifier for treating a patient, comprising, two major particle populations, one such population being of lesser size particles comprised of ribosomes and the other such population being comprised of natural membrane vesicles having a mean diameter in excess of 180 nm, in a suspending buffer, said membrane vesicles and ribosomes both being endogenous to the same selected microorganism which does not evoke a significant immune deviating response in the patient and which is substantially nonpathogenic in humans, said selected microorganisms also being one in which membrane vesicles are capable of being formed from cell membrane material, said vesicles being readily endocytosed by the monocyte-macrophage cell line of the patient, said biologic response modifier being substantially free of intact cells, and having tolerable levels of endotoxin, cell walls, and cell membrane fragments, said biologic response modifier exhibiting in vitro induction of human natural killer cells at a level substantially equivalent to or better than leukocyte interferon for effector to target cell ratios exceeding 25:1.

2. A biologic response modifier according to claim 1 wherein each of said populations is represented by substantially distinct peaks on a size distribution curve upon particle size analysis.

3. A biologic response modifier according to claim 1 wherein substantially all of said natural membrane vesicles have a diameter exceeding 100 nm.

4. A biologic response modifier according to claim 1 demonstrating a detectable activation of the monocyte-macrophage cell line of the patient.

5. A biologic response modifier according to claim 1 wherein said predetermined microorganism is selected from the group consisting of *Serratia marcescens, Erwinia chrysanthemi* and *Enterobacter aerogenes.*

6. A biologic response modifier comprising membrane vesicles and ribosomes in a suspending buffer, said membrane vesicles being comprised of cellular membrane material endogenous to the organism *Serratia marcescens,* said ribosomes also being endogenous to the organism *Serratia marcescens,* said membrane vesicles having a mean diameter of at least 180 nm, said biologic response modifier being substantially free of intact cells, and having tolerable levels of endotoxin, cell walls, and cell membrane fragments, said biologic response modifier exhibiting in vitro induction of human natural killer cells at a level substantially equivalent to or better than leukocyte interferon for effector to target cell ratios exceeding 25:1.

7. A biologic response modifier according to claim 6 demonstrating a detectable activation of the monocyte-macrophage cell line.

8. A biologic response modifier according to claim 6 wherein substantially all of said vesicles exceed 110 nm in diameter.

9. A biologic response modifier for treating a patient, comprising, two major particle populations, one such population being of lesser size particles comprised of ribosomes and the other such population being comprised of natural membrane vesicles having a mean diameter in excess of 180 nm., in a suspending buffer, said membrane vesicles and ribosomes both being endogenous to the same selected microorganism which does not evoke a significant immune deviating response in the patient and which is substantially nonpathogenic in humans, said selected microorganism also being one in which membrane vesicles are capable of being formed from cell membrane material, said vesicles being readily endocytosed by the monocyte-macrophage cell line of the patient, said biologic response modifier being substantially free of intact cells, and having tolerable levels of endotoxin, cell walls, and cell membrane fragments.

* * * * *

UNITED STATES PATENT AND TRADEMARK OFFICE
CERTIFICATE OF CORRECTION

PATENT NO. : 4,971,801
DATED : November 20, 1990
INVENTOR(S) : Richard W. Urban It is certified that error appears in the above-identified patent and that said Letters Patent is hereby corrected as shown below:

Column 1, line 65, delete "2-51." and insert therefore --.2-51--.

Column 1, line 36, "Corynebacteria, Mycobacteria and Nocardia" should be --*Corynebacteria, Mycobacteria* and *Norcardia*--.

Column 2, line 51, after "has" insert --thus--.

Column 3 lines 36, 39 and 41, "in vivo" should be --*in vivo*--.

Column 3 lines 47, 48 and 49, "in vivo" should be --*in vivo*--.

Column 3 lines 47, 48 and 49, "in vitro" should be --*in vitro*--.

Column 4, line 18, "in vivo" should be --*in vivo*--.

Column 5, line 12, "in vitro" should be --*in vitro*--.

Column 5, line 16, delete "have" and insert therefore --has--.

Column 6, line 5, after "processed" insert --)--.

Column 6, line 46, delete "50" and insert therefore --500--.

Column 7, line 5, "50" should not be bolded.

Column 8, line 9, delete "said" and insert therefore --and--.

Column 8, line 26, after "600" insert --.--.

Column 8, line 34, delete "[" and insert therefore --(--.

Column 8, line 60, "not" should be --*not*--.

UNITED STATES PATENT AND TRADEMARK OFFICE
CERTIFICATE OF CORRECTION

PATENT NO. : 4,971,801

DATED : November 20, 1990

INVENTOR(S) : Richard W. Urban

It is certified that error appears in the above-identified patent and that said Letters Patent is hereby corrected as shown below:

Column 9, line 8, "Limulus" should be --*Limulus*--.

Column 9, line 11, delete "," and insert therefore --;--.

Column 9, line 19, "Limulus" should be --*Limulus*--.

Column 9, line 32, "Limulus" should be --*Limulus*--.

Column 9, line 36, after "deceleration" insert --.--.

Column 9, line 40, "Limulus" should be --*Limulus*--.

Column 10, line 4, after "minutes" insert --#--.

Column 10, line 68, after "TABLE 1" one whole paragraph is missing. Accordingly, insert --Means weights for 100 µg group at $t_0$ and 24 hours post-injection were 1.72 g and 2.94 g respectively. Mean weights for 200 µg group at $t_0$, 24 hours and 6 days post-injection were 1.57 g, 2.16 g and 4.5 g respectively.--.

Column 12, line 16, "in vitro" should be --*in vitro*--.

Column 12, line 42, "in vitro" should be --*in vitro*--.

Column 14, line 23, "in vitro" should be --*in vitro*--.

Column 15, line 61, "13/" should be superscripted.

Column 16, line 28, "in vivo" should be --*in vivo*--.

Column 17, line 11, delete "receiVed" and insert therefore --received--.

UNITED STATES PATENT AND TRADEMARK OFFICE
CERTIFICATE OF CORRECTION

PATENT NO. : 4,971,801

DATED : November 20, 1990

INVENTOR(S) : Richard W. Urban

It is certified that error appears in the above-identified patent and that said Letters Patent is hereby corrected as shown below:

Column 17, line 19, "in vivo" should be --*in vivo*--.

Column 17, lines 34-35, lines should not be indented.

Column 19, line 28, "in vitro" should be --*in vitro*--.

Column 19, line 32, "in vitro" should be --*in vitro*--.

Column 19, line 36, "in vitro" should be --*in vitro*--.

Column 19, line 39, "in vitro" should be --*in vitro*--.

Column 19, line 43, "in vitro" should be --*in vitro*--.

Column 19, line 49, "in vitro" should be --*in vitro*--.

Column 19, line 52, "in vitro" should be --*in vitro*--.

Column 19, line 58, "in vitro" should be --*in vitro*--.

Column 20, line 2, delete "produce" and insert therefore --product--.

Column 20, line 3, "in vivo" should be --*in vivo*--.

Column 20, line 4, "in vitro" should be --*in vitro*--.

Column 20, line 7, "in vitro" should be --*in vitro*--.

Column 20, line 15, "in vivo" should be --*in vivo*--.

Column 20, line 16, "in vitro" should be --*in vitro*--.

Column 20, line 23, "12" should be --12--.

UNITED STATES PATENT AND TRADEMARK OFFICE
CERTIFICATE OF CORRECTION

PATENT NO. : 4,971,801

DATED : November 20, 1990

INVENTOR(S) : Richard W. Urban

It is certified that error appears in the above-identified patent and that said Letters Patent is hereby corrected as shown below:

Column 20, line 36, "Serratia" should be --*Serratia*--.

Column 21, line 27, "in vitro" should be --*in vitro*--.

Column 21, line 58, "14:929-14 933" should be --14:929-933--.

Column 21, line 60, footnote 3 should be on next line.

Column 21, line 67, "et al." should be --*et al.*--.

Column 22, line 23, footnote 13 should be indented.

Column 22, line 29, footnote 14 should be on next line and indented.

Column 22, line 30, footnote 15 should be on next line and indented.

Column 22, lines 50-51, "in vitro" should be --*in vitro*--.

Column 23, line 14, "in vitro" should be --*in vitro*--.

UNITED STATES PATENT AND TRADEMARK OFFICE
CERTIFICATE OF CORRECTION

PATENT NO. : 4,971,801
DATED : November 20, 1990
INVENTOR(S) : Richard W. Urban

It is certified that error appears in the above-indentified patent and that said Letters Patent is hereby corrected as shown below:

Column 10, lines 36-37, after "1.0-1.2" insert --mg --.
Column 10, lines 36-37, after "acid" delete --mg --.
Column 10, line 37, after "per" delete "0" and insert therefore --1.0 --.

Signed and Sealed this

Twenty-first Day of February, 1995

Attest:

BRUCE LEHMAN

Attesting Officer   Commissioner of Patents and Trademarks